United States Patent
Ding et al.

(10) Patent No.: US 10,595,933 B2
(45) Date of Patent: Mar. 24, 2020

(54) MULTIFUNCTIONAL VESSEL SEALING AND DIVIDER DEVICE

(71) Applicant: COVIDIEN LP, Mansfield, MA (US)

(72) Inventors: Weijiang Ding, Shanghai (CN); Kai Liu, Hunan (CN)

(73) Assignee: COVIDIEN LP, Mansfield, MA (US)

( * ) Notice: Subject to any disclaimer, the term of this patent is extended or adjusted under 35 U.S.C. 154(b) by 87 days.

(21) Appl. No.: 15/567,107

(22) PCT Filed: Apr. 24, 2015

(86) PCT No.: PCT/CN2015/077339
§ 371 (c)(1),
(2) Date: Oct. 17, 2017

(87) PCT Pub. No.: WO2016/169038
PCT Pub. Date: Oct. 27, 2016

(65) Prior Publication Data
US 2018/0103995 A1    Apr. 19, 2018

(51) Int. Cl.
*A61B 18/14* (2006.01)
*A61B 17/285* (2006.01)
(Continued)

(52) U.S. Cl.
CPC .......... *A61B 18/1445* (2013.01); *A61B 17/28* (2013.01); *A61B 17/282* (2013.01);
(Continued)

(58) Field of Classification Search
CPC . A61B 17/29; A61B 17/2812; A61B 18/1442; A61B 2018/00607;
(Continued)

(56) References Cited

U.S. PATENT DOCUMENTS

D249,549 S   9/1978 Pike
D263,020 S   2/1982 Rau, III
(Continued)

FOREIGN PATENT DOCUMENTS

CN   201299462 Y   9/2009
DE   2415263 A1   10/1975
(Continued)

OTHER PUBLICATIONS

Heniford et al. "Initial Research and Clinical Results with an Electrothermal Bipolar Vessel Sealer" Oct. 1999.
(Continued)

*Primary Examiner* — Michael F Peffley
*Assistant Examiner* — Amanda L Zink
(74) *Attorney, Agent, or Firm* — Carter, DeLuca & Farrell LLP

(57) ABSTRACT

An electrosurgical forceps includes an end effector including a first jaw member having a proximal portion including a first jaw guide member and a distal portion including a first tissue contacting surface, and a second jaw member having a proximal portion including a second jaw guide member and a distal portion including a second tissue contacting surface. The first and second tissue contacting surfaces each include a shear edge disposed between stepped surfaces. The jaw members are vertically movable between an open position and a first approximated position in which the tissue contacting surfaces vertically oppose and laterally align with each other, and laterally movable between the first approximated position and a second approximated position to laterally displace the tissue contacting surfaces with respect to each other. The jaw guide members control an open angle between the jaw members during movement between the first and second approximated positions.

16 Claims, 14 Drawing Sheets

(51) Int. Cl.
*A61B 17/28* (2006.01)
*A61B 18/00* (2006.01)
*A61B 34/30* (2016.01)

(52) U.S. Cl.
CPC ........ *A61B 17/285* (2013.01); *A61B 17/2833* (2013.01); *A61B 18/1442* (2013.01); *A61B 17/2812* (2013.01); *A61B 34/30* (2016.02); *A61B 2018/0063* (2013.01); *A61B 2018/00607* (2013.01)

(58) Field of Classification Search
CPC ...... A61B 2018/146; A61B 2018/1452; A61B 2017/2808; A61B 2017/2947; A61B 17/28; A61B 17/282; A61B 17/2833; A61B 17/285; A61B 18/1445; A61B 2018/0063; A61B 34/30
See application file for complete search history.

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |
| 9,084,608 B2 | 7/2015 | Larson et al. | |
| 9,211,657 B2 | 12/2015 | Ackley et al. | |
| 2004/0006340 A1* | 1/2004 | Latterell | A61B 18/1442 606/48 |
| 2009/0209991 A1* | 8/2009 | Hinchliffe | A61B 17/1608 606/170 |
| 2013/0304114 A1* | 11/2013 | Joseph | A61B 17/285 606/205 |
| 2014/0221995 A1 | 8/2014 | Guerra et al. | |
| 2014/0221999 A1 | 8/2014 | Cunningham et al. | |
| 2014/0228842 A1 | 8/2014 | Dycus et al. | |
| 2014/0230243 A1 | 8/2014 | Roy et al. | |
| 2014/0236149 A1 | 8/2014 | Kharin et al. | |
| 2014/0243811 A1 | 8/2014 | Reschke et al. | |
| 2014/0243824 A1 | 8/2014 | Gilbert | |
| 2014/0249528 A1 | 9/2014 | Hixson et al. | |
| 2014/0250686 A1 | 9/2014 | Hempstead et al. | |
| 2014/0257274 A1 | 9/2014 | McCullough, Jr. et al. | |
| 2014/0257283 A1 | 9/2014 | Johnson et al. | |
| 2014/0257284 A1 | 9/2014 | Artale | |
| 2014/0257285 A1 | 9/2014 | Moua | |
| 2014/0276803 A1 | 9/2014 | Hart | |
| 2014/0284313 A1 | 9/2014 | Allen, IV et al. | |
| 2014/0288549 A1 | 9/2014 | McKenna et al. | |
| 2014/0288553 A1 | 9/2014 | Johnson et al. | |
| 2014/0330308 A1 | 11/2014 | Hart et al. | |
| 2014/0336635 A1 | 11/2014 | Hart et al. | |
| 2014/0353188 A1 | 12/2014 | Reschke et al. | |
| 2015/0018816 A1 | 1/2015 | Latimer | |
| 2015/0025528 A1 | 1/2015 | Arts | |
| 2015/0032106 A1 | 1/2015 | Rachlin | |
| 2015/0051598 A1 | 2/2015 | Orszulak et al. | |
| 2015/0051640 A1 | 2/2015 | Twomey et al. | |
| 2015/0066026 A1 | 3/2015 | Hart et al. | |
| 2015/0080880 A1 | 3/2015 | Sartor et al. | |
| 2015/0080889 A1 | 3/2015 | Cunningham et al. | |
| 2015/0082928 A1 | 3/2015 | Kappus et al. | |
| 2015/0088122 A1 | 3/2015 | Jensen | |
| 2015/0088126 A1 | 3/2015 | Duffin et al. | |
| 2015/0088128 A1 | 3/2015 | Couture | |
| 2015/0094714 A1 | 4/2015 | Lee et al. | |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |

(56) References Cited

FOREIGN PATENT DOCUMENTS

| | | |
|---|---|---|
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/ Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

(56) References Cited

OTHER PUBLICATIONS

Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).
Oulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler, Abandoned.
U.S. Appl. No. 09/177,950, filed Oct. 23, 1998; inventor: Randel A. Frazier, abandoned.
U.S. Appl. No. 09/387,883, filed Sep. 1, 1999; inventor: Dale F. Schmaltz, abandoned.
U.S. Appl. No. 09/591,328, filed Jun. 9, 2000; inventor: Thomas P. Ryan, abandoned.
U.S. Appl. No. 12/336,970, filed Dec. 17, 2008; inventor: Paul R. Sremcich, abandoned.
U.S. Appl. No. 14/065,644, filed Oct. 29, 2013; inventor: Reschke, abandoned.

* cited by examiner

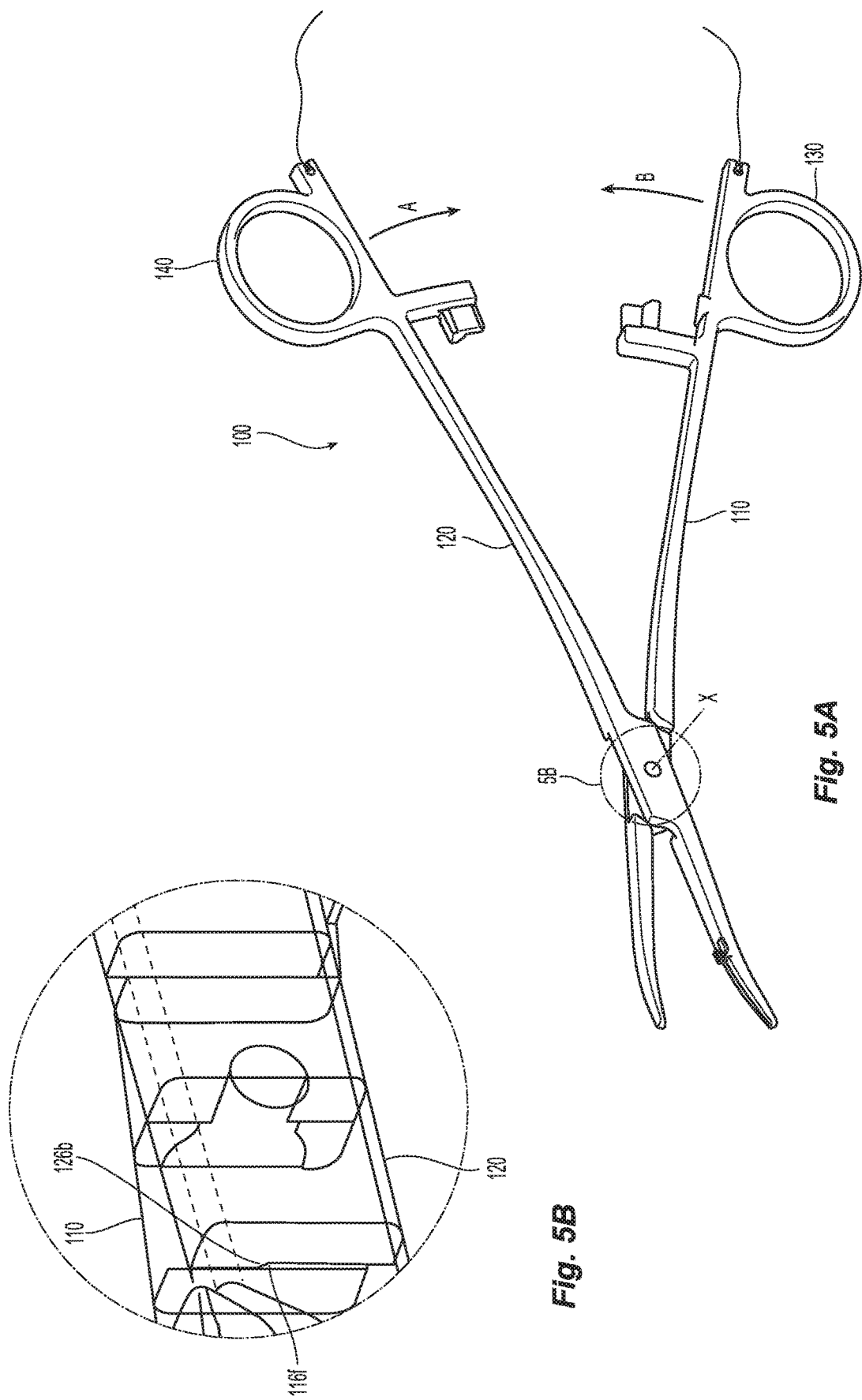

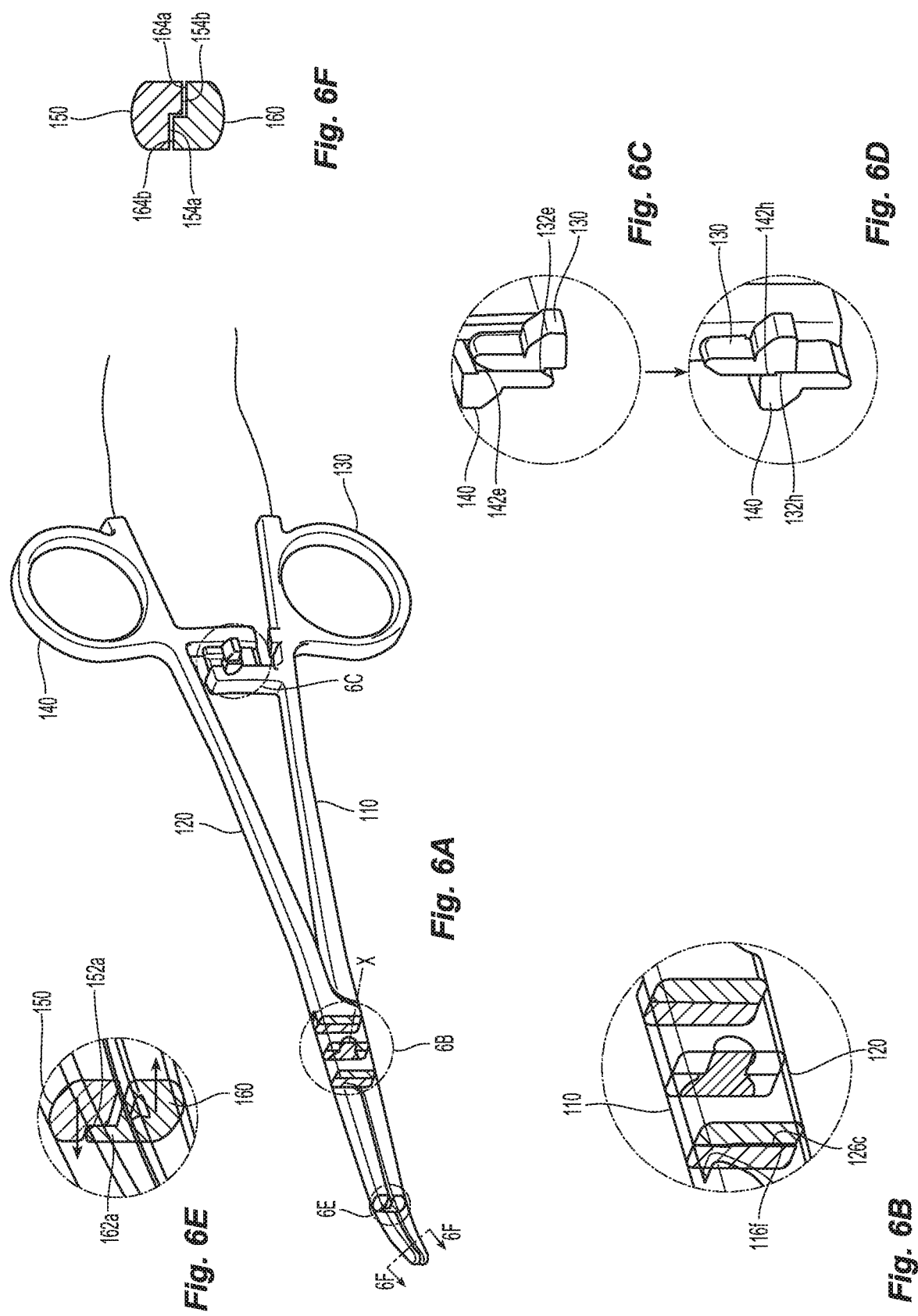

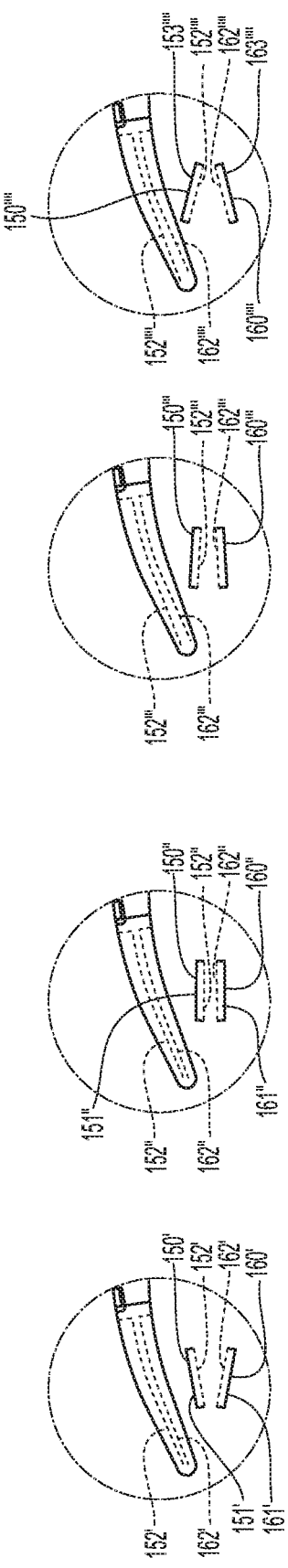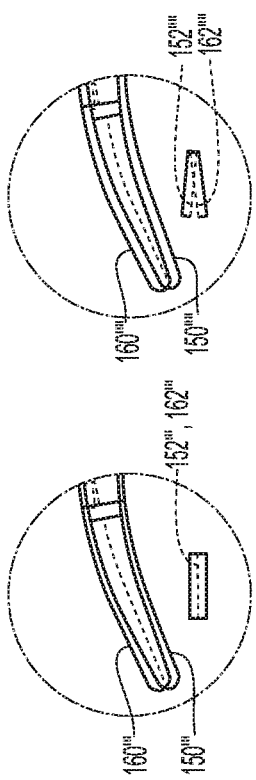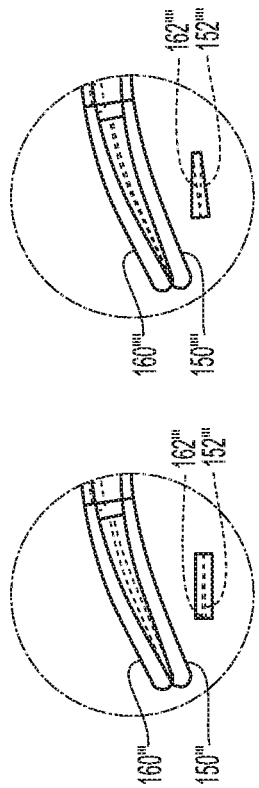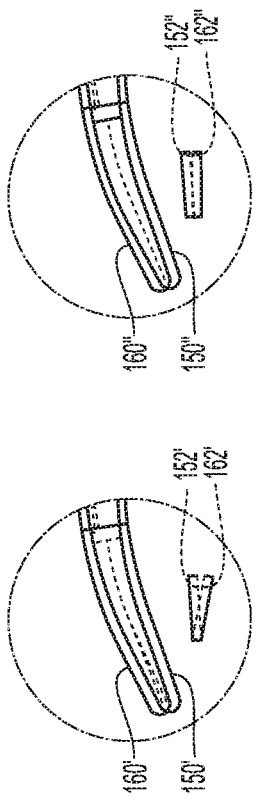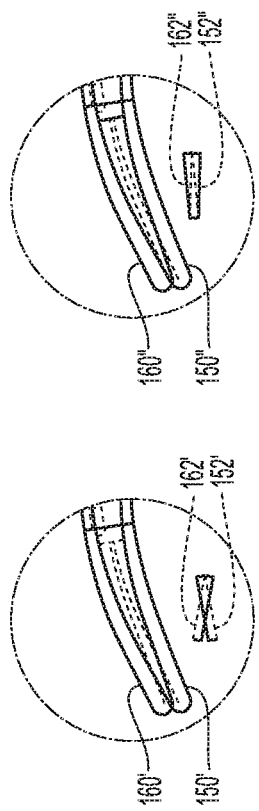

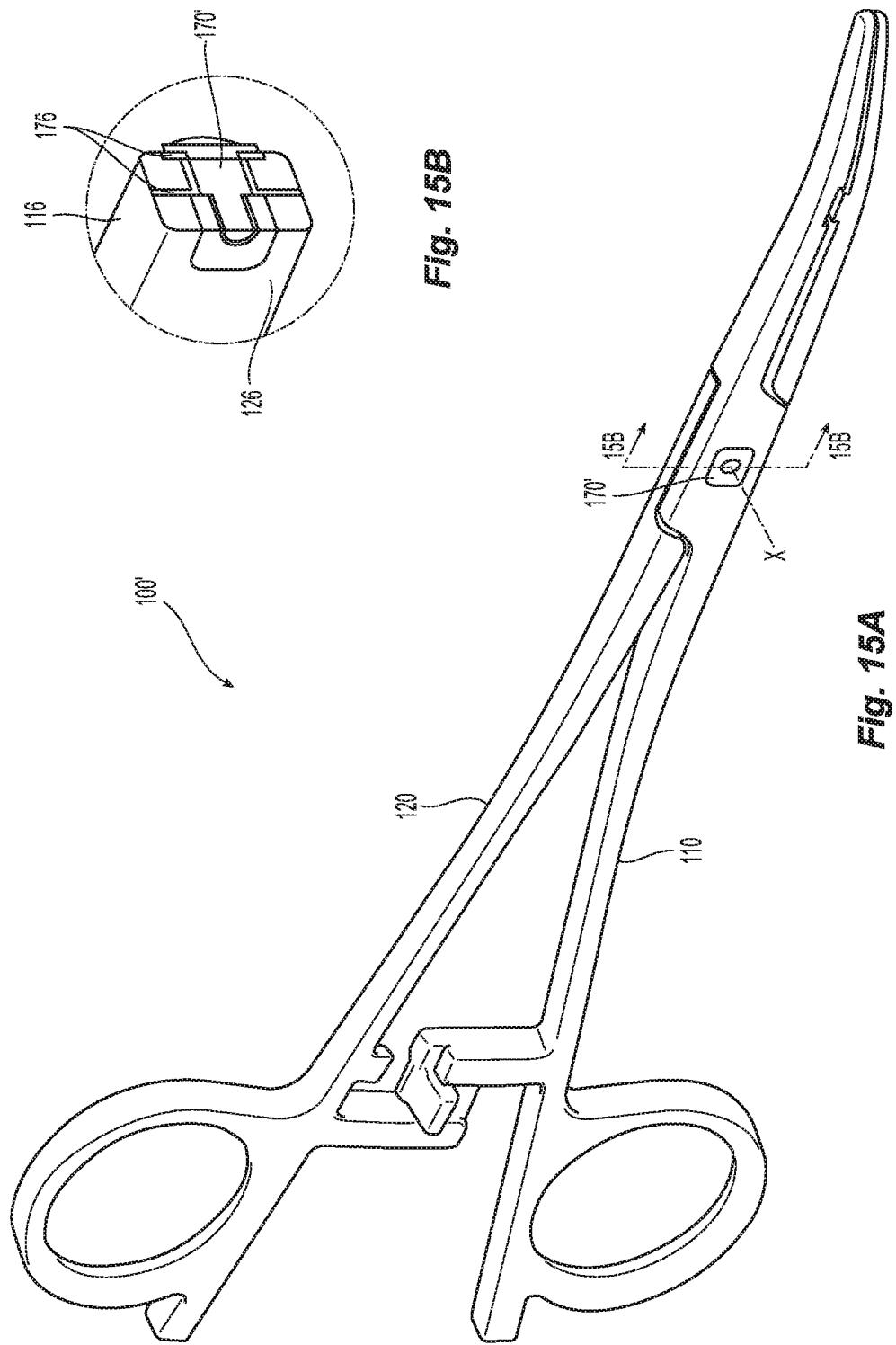

MULTIFUNCTIONAL VESSEL SEALING AND DIVIDER DEVICE

CROSS REFERENCE TO RELATED APPLICATION

The present application is a U.S. National Stage Application under 35 U.S.C. § 371(a) of PCT/CN2015/077339 filed Apr. 24, 2015, the entire contents of which are incorporated by reference herein.

BACKGROUND

1. Background of Related Art

The present disclosure relates to energy-based surgical instruments and, more particularly, to energy-based surgical forceps configured for treating and/or cutting tissue.

2. Technical Field

A forceps or hemostat is a plier-like instrument which relies on mechanical action between its jaws to grasp, clamp, and constrict tissue. Energy-based forceps utilize both mechanical clamping action and energy, e.g., electrosurgical energy, ultrasonic energy, light energy, microwave energy, heat, etc., to affect hemostasis by heating tissue to coagulate and/or cauterize tissue. Certain surgical procedures require more than simply cauterizing tissue and rely on the unique combination of clamping pressure, precise energy control, and gap distance (i.e., distance between opposing jaws when closed about tissue) to "seal" tissue. Typically, once tissue is sealed, the surgeon has to accurately sever the tissue along the newly formed tissue seal. Accordingly, many tissue sealing instruments have been designed to incorporate a blade that is movable with respect to a blade slot disposed in a jaw of the tissue sealing instrument to sever the tissue after forming a tissue seal.

Tissue sealing instruments that include a blade and blade slot, however, are typically single-use devices as the blade and blade slot may be difficult to clean, and the blade may wear and dull with repeated use. The incorporation of a blade slot into a jaw of a tissue sealing instrument may reduce the sealing strength of the jaw, and the width of the blade slot may increase the width of the jaw which, in turn, may result in a reduction in the dissection capabilities of the tissue sealing instrument. Accordingly, such tissue sealing instruments may be suitable for blunt dissection, and a separate instrument, such as shears, may be needed for sharp dissection of tissues and/or vessels.

SUMMARY

The present disclosure is directed to reusable energy-based surgical instruments having movable, opposed jaw members that are configured for grasping, sealing, and blunt and fine dissecting of tissue.

In accordance with aspects of the present disclosure, an electrosurgical forceps includes an end effector including first and second jaw members. The first jaw member has a proximal portion including a first jaw guide member and a distal portion including a first tissue contacting surface. The second jaw member has a proximal portion including a second jaw guide member and a distal portion including a second tissue contacting surface. Each of the first and second tissue contacting surfaces have a shear edge disposed between stepped surfaces. The first and second jaw members are vertically movable between an open position and a first approximated position in which the first and second tissue contacting surfaces vertically oppose and laterally align with each other, and laterally movable between the first approximated position and a second approximated position to laterally displace the first and second tissue contacting surfaces with respect to each other. The first and second jaw guide members control an open angle between the first and second jaw members during movement between the first approximated position and the second approximated position to aid in cutting tissue disposed therebetween.

In embodiments, the stepped surface of each of the first and second tissue contacting surfaces includes a base surface laterally disposed relative to a raised surface. The base and raised surfaces are connected by an intermediate wall that forms the shear edge at an intersection with the raised surface. In some embodiments, the distal portions of the first and second jaw members curve longitudinally and laterally away from the proximal portions of the first and second jaw members.

In embodiments, the first and second guide surfaces include opposed oblique walls that slide laterally relative to each other during movement from the first approximated position to the second approximated position. In some embodiments, the proximal portion of the first jaw member includes a slot defined in an outer edge thereof and the proximal portion of the second jaw member includes a complementary tab for reception within the slot.

The electrosurgical forceps may further include first and second elongated shaft members that cooperate to define the end effector. The first jaw member is disposed on a distal end portion of the first elongated shaft member and the second jaw member is disposed on a distal end portion of the second elongated shaft member. The first and second elongated shaft members are coupled together by a pivot pin extending through openings defined in respective first and second intersection portions of the first and second elongated shaft members. At least one of the first and second elongated shaft members is pivotable with respect to the other of the first and second shaft members about at least two axes.

In some embodiments, the pivot pin includes a semi-spherical head disposed within the opening defined in the first intersection portion and a cylindrical shaft extending through the opening defined in the second intersection portion. In some embodiments, the pivot pin includes a hemi-cylindrical head disposed within the opening defined in the first intersection portion and a cylindrical shaft extending through the opening defined in the second intersection portion.

In embodiments, the first intersection portion includes an inner surface having a substantially flat proximal portion, an oblique distal portion, and a convex portion disposed at a distal end of the oblique distal portion, and the second intersection portion includes a substantially flat inner surface and a concave surface disposed at a distal end of the substantially flat inner surface. In some embodiments, the first intersection portion includes a cam face disposed between the substantially flat proximal portion and the oblique distal portion.

Proximal end portions of the first and second elongated shaft members may include first and second handle members, respectively. The first handle member includes a first guide member and the second handle member includes a second guide member. Each of the first and second guide members includes a body portion extending generally vertically from an inner surface of the respective first and second handle member, a leg portion extending substantially perpendicularly from the body portion, and a gap defined between an upper surface of the leg portion and the inner surface of the respective first and second handle member. The leg portions of the first and second guide members are longitudinally aligned and laterally offset with respect to each another.

In embodiments, when the first and second handle members are in the open position the first and second guide members are spaced apart, and when the first and second handle members are in the first approximated position, the inner surfaces of the leg portions of the first and second guide members contact with each other. In some embodiments, when the first and second handle members are in the first approximated position, the inner surfaces of the legs portions of the first and second guide members are locked relative to each other. In some embodiments, when the first and second handle members are in the first approximated position, a bottom surface of the body portion of the first guide member contacts an inner surface of the second elongated shaft member. In embodiments, when the first and second handle members are in the second approximated position, the upper surfaces of the leg portions of the first and second guide members contact each other. In embodiments, outer surfaces of the leg portions of the first and second guide members each include a protrusive surface to prevent movement of the first and second handle members from the open position to the first approximated position when the outer surfaces are aligned with each other.

In accordance with aspects of the present disclosure, a method of treating tissue includes: vertically moving at least one of first and second handle members of an electrosurgical forceps towards the other of the first and second handle members to move first and second jaw members of the electrosurgical forceps from an open position to a first approximated position in which first and second tissue contacting surfaces are opposed and substantially aligned with each other to grasp tissue therebetween; and laterally moving at least one of the first and second handle members towards the other of the first and second handle members from the first approximated position to a second approximated position to cut tissue disposed between the first and second jaw members by crossing shear edges defined on the first and second tissue contacting surfaces.

BRIEF DESCRIPTION OF THE DRAWINGS

Various aspects and features of the present disclosure are described herein with reference to the drawings wherein corresponding reference characters indicate corresponding parts throughout the drawings, and wherein:

FIG. 5A is a side, perspective view of the forceps of FIG. 1 during movement from an open position towards a first approximated position;

FIG. 5B is an enlarged view of a portion of the forceps of FIG. 5A shown along the area of detail 5B identified in FIG. 5A;

FIG. 6A is a side, perspective view of the forceps of FIG. 1 in a first approximated position;

FIG. 6B is an enlarged view of a portion of the forceps of FIG. 6A shown along the area of detail 6B identified in FIG. 6A;

FIG. 6C is an enlarged view of a portion of the forceps of FIG. 6A shown along the area of detail 6C identified in FIG. 6A during movement towards the first approximated position;

FIG. 6D is an enlarged view of the portion of the forceps shown in FIG. 6C in a locked state in the first approximated position;

FIG. 6E is an enlarged view of a portion of the forceps of FIG. 6A shown along the area of detail 6E identified in FIG. 6A;

FIG. 6F is a cross-sectional view a portion of the forceps of FIG. 6A taken along line 6F-6F of FIG. 6A;

FIGS. 10A-10C are top and side views of jaw members of a forceps in accordance with another embodiment of the present disclosure in a first approximated position, during movement from the first approximated position to a second approximated position, and in the second approximated position, respectively;

FIGS. 11A-11C are top and side views of jaw members of a forceps in accordance with yet another embodiment of the present disclosure in a first approximated position, during movement from the first approximated position to a second approximated position, and in the second approximated position, respectively;

FIGS. 12A-12C are top and side views of jaw members of a forceps in accordance with another embodiment of the present disclosure in a first approximated position, during movement from the first approximated position to a second approximated position, and in the second approximated position, respectively;

FIGS. 13A-13C are top and side views of jaw members of a forceps in accordance with another embodiment of the present disclosure in a first approximated position, during movement from the first approximated position to a second approximated position, and in the second approximated position, respectively;

FIG. 15A is a side, perspective view of a forceps in accordance with another embodiment of the present disclosure;

FIG. 15B is a perspective cross-sectional view of a portion of the forceps of FIG. 15A taken along line 15B-15B of FIG. 15A;

DETAILED DESCRIPTION

Figure 1:
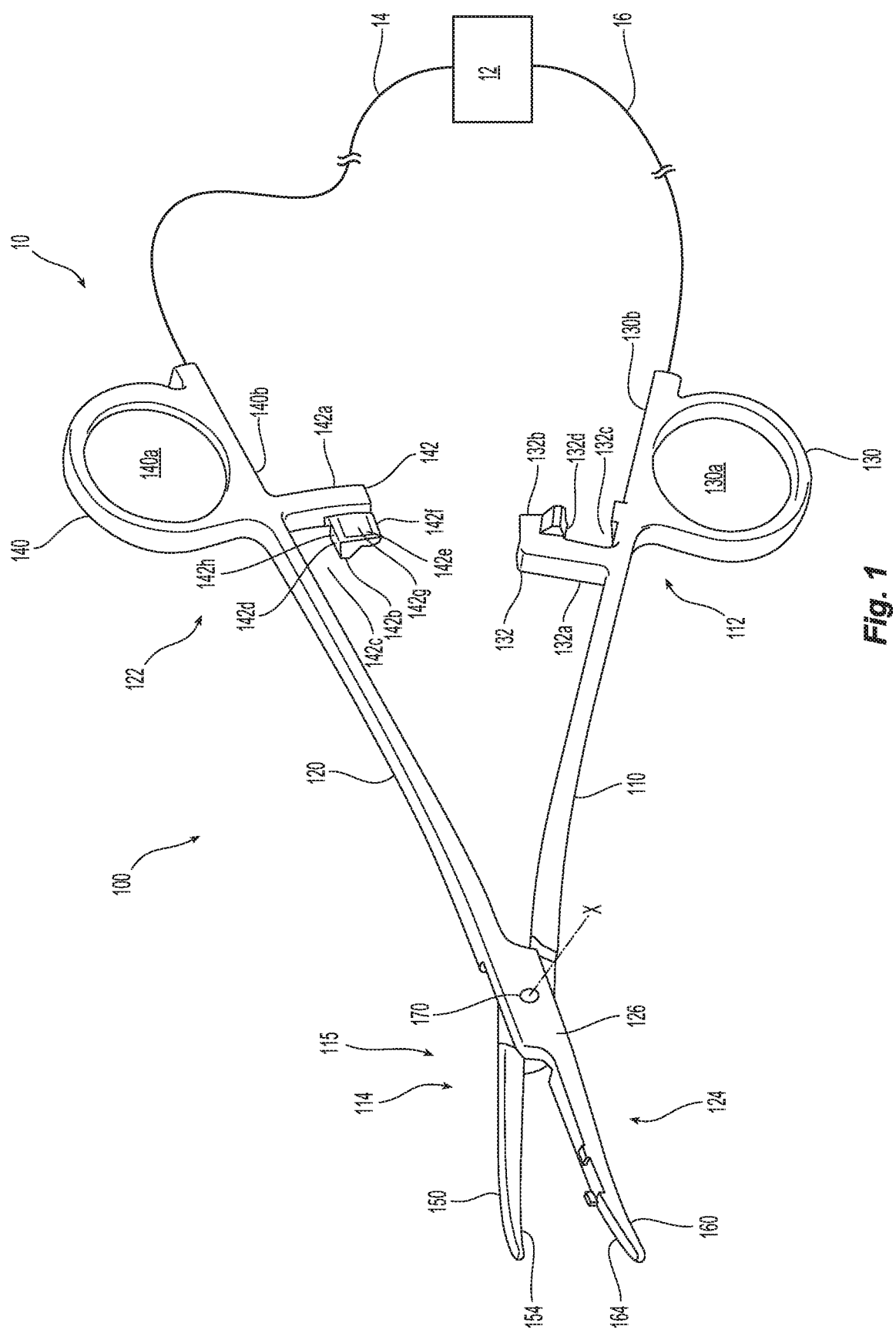
FIG. 1 is a side, perspective view of a surgical system including an open electrosurgical forceps connected to an electrosurgical energy source in accordance with an embodiment of the present disclosure.

In this disclosure, the term "proximal" refers to a portion of a structure closer to an operator, while the term "distal" refers to a portion of the same structure further from the operator. As used herein, the term "subject" refers to a human patient or animal. The term "operator" refers to a doctor (e.g., a surgeon), a nurse, and other clinicians or care providers, and may include support personnel. The terms "generally," "substantially," and "about" shall be understood as words of approximation that take into account relatively little to no variation in the modified term(s). Reference terms, such as "horizontal," "vertical," "upper," "lower," "above," "below," and the like, are intended to ease description of the embodiments and are not intended to have any limiting effect on the ultimate orientations of the surgical instruments, or any parts thereof.

Referring now to FIGS. 1-4, an energy-based surgical system 10 in accordance with the present disclosure is configured for grasping, electrically sealing, mechanically cutting, and dissecting tissue and/or vessels in open and/or laparoscopic surgical procedures. The energy-based surgical system 10 includes a reusable forceps 100 releasably connected to an electrosurgical energy source 12 via cable 14 and 16.

The forceps 100 includes a first elongated shaft member 110 pivotably coupled to a second elongated shaft member 120. The first elongated shaft member 110 includes proximal and distal end portions 112 and 114, respectively, and the second elongated shaft member 120 includes proximal and distal end portions 122 and 124, respectively. The proximal end portions 112 and 122 of the first and second shaft members 110 and 120 include first and second handle members 130 and 140, respectively. The first and second handle members 130 and 140 are configured to allow an operator to effect movement of at least one of the first and second shaft members 110 and 120 relative to the other. The distal end portions 114 and 124 of the first and second shaft members 110 and 120 cooperate to define an end effector assembly 115 having opposed first and second jaw members 150 and 160.

The first and second handle members 130 and 140 each define a finger hole 130a and 140a, respectively, therethrough for receiving a finger of an operator. The finger holes 130a and 140a facilitate movement of the first and second handle members 130 and 140 relative to each other. The first and second handle members 130 and 140 are each monolithically formed with its respective shaft member 110 and 120. Alternatively, the first and second handle members 130 and 140 may each be engaged with its respective shaft member 110 and 120 in any suitable configuration, e.g., via mechanical engagement, molding, adhesion, etc.

The first handle member 130 includes a first guide member 132 extending from an inner surface 130b of the first handle member 130 towards the second handle member 140. The first guide member 132 includes a body portion 132a extending generally vertically towards the second handle member 140 and a leg portion 132b extending substantially perpendicularly from the body portion 132a such that the body portion 132a and the leg portion 132b have a general L-shaped configuration and define a gap 132c between the inner surface 130b of the first handle member 130 and an upper surface 132d of the leg portion 132b of the first guide member 132. The leg portion 132b includes an inner surface 132e (see e.g., FIG. 2) having a curved lower surface 132f, a substantially flat intermediate surface 132g, and a recessed upper surface 132h. The leg portion 132b also includes an outer surface 132i (see e.g., FIG. 3) having a substantially flat lower surface 132j and a protrusive upper surface 132k.

Similarly, the second handle member 140 includes a second guide member 142 extending from an inner surface 140b of the second handle member 140 towards the first handle member 130. The second guide member 142 includes a body portion 142a extending generally vertically towards the second handle member 140 and a leg portion 142b extending substantially perpendicularly from the body portion 142a such that the body portion 142a and the leg portion 142b have a general L-shaped configuration and define a gap 142c between the inner surface 140b of the first second member 140 and an upper surface 142d of the leg portion 142b of the second guide member 142. The leg portion 142b includes an inner surface 142e having a curved lower surface 142f, a substantially flat intermediate surface 142g, and a recessed upper surface 142h. The leg portion 142b also includes an outer surface 142i (see e.g., FIG. 2) having a substantially flat lower surface 142j and a protrusive upper surface 142k.

The first and second guide members 132 and 142 are disposed on the first and second handle members 130 and 140 with the body portions 132a and 142a longitudinally offset and laterally spaced with respect to one another and the leg portions 132b and 142b aligned such that the leg portions 132b and 142b interact with each other upon movement of the first and second handle members 130 and 140, as described in further detail below.

Figure 3:
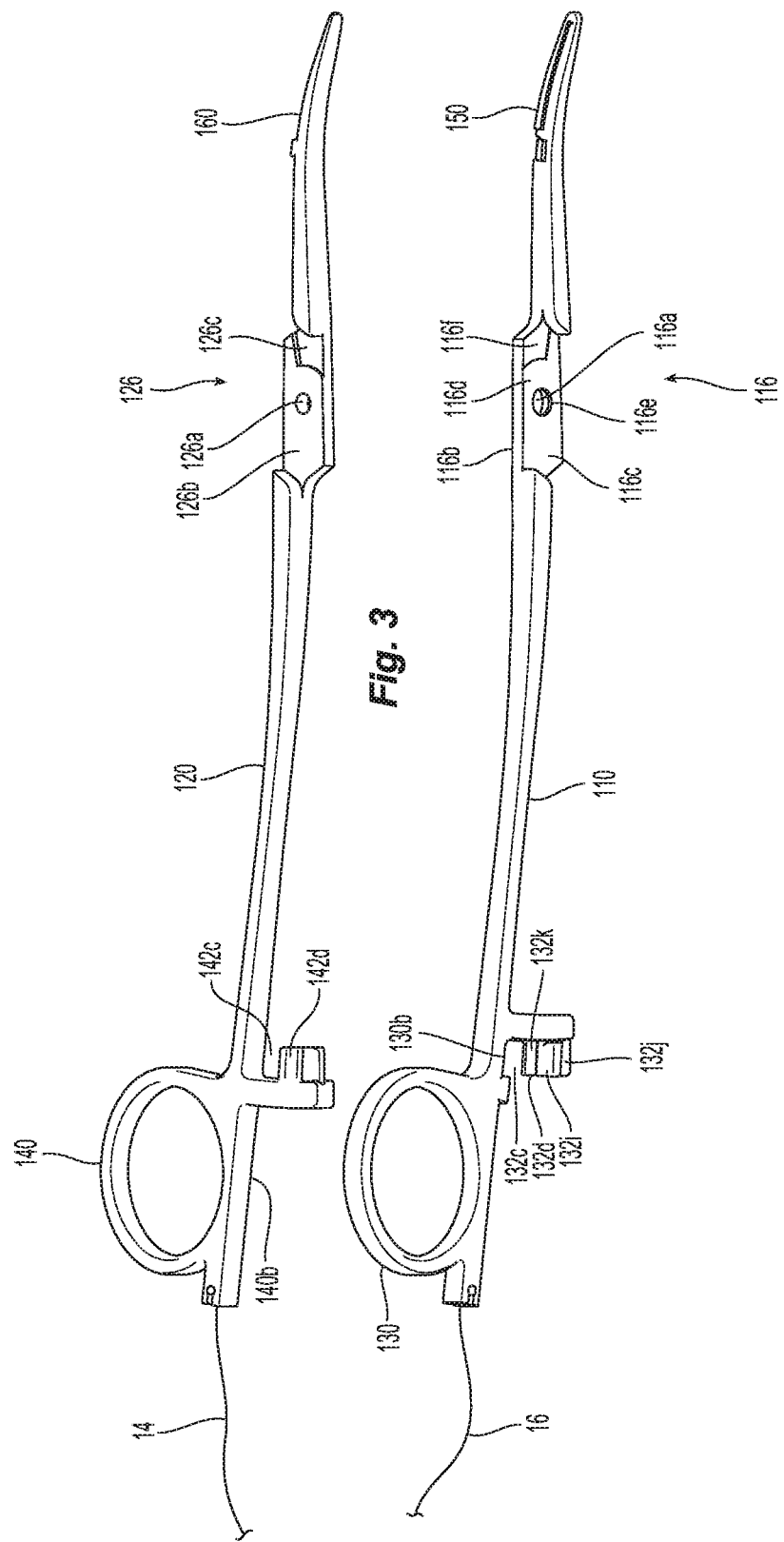
FIG. 3 is a perspective view of inner surfaces of first and second elongated shaft members of the forceps of FIG. 2.

The first shaft member 110 intersects the second shaft member 120 at intersection portions 116 and 126 of the first and second shaft members 110 and 120, respectively. The intersection portion 116 of the first shaft member 110 defines an opening 116a therethrough. As best seen in FIG. 3, an inner surface 116b of the intersection portion 116 includes a substantially flat proximal portion 116c, an oblique distal portion 116d, a cam face 116e disposed at the intersection of the proximal portion 116c with the distal portion 116d, and a convex plate 116f attached to a distal end of the distal portion 116d.

As best seen in FIG. 3, the intersection portion 126 of the second shaft member 120 includes an opening 126a defined through a substantially flat inner surface 126b of the intersection portion 126 and a concave plate 126c attached to a distal end of the inner surface 126b that is complementary in shape with the convex plate 116f of the intersection portion 116 of the first shaft member 110. It should be understood that in lieu of the convex and concave plates 116f and 126c, the inner surfaces 116b and 126b of the intersection portions 116 and 126 may be contoured to include surface geometries corresponding to that of the convex and concave plates 116f and 126c.

Figure 2:
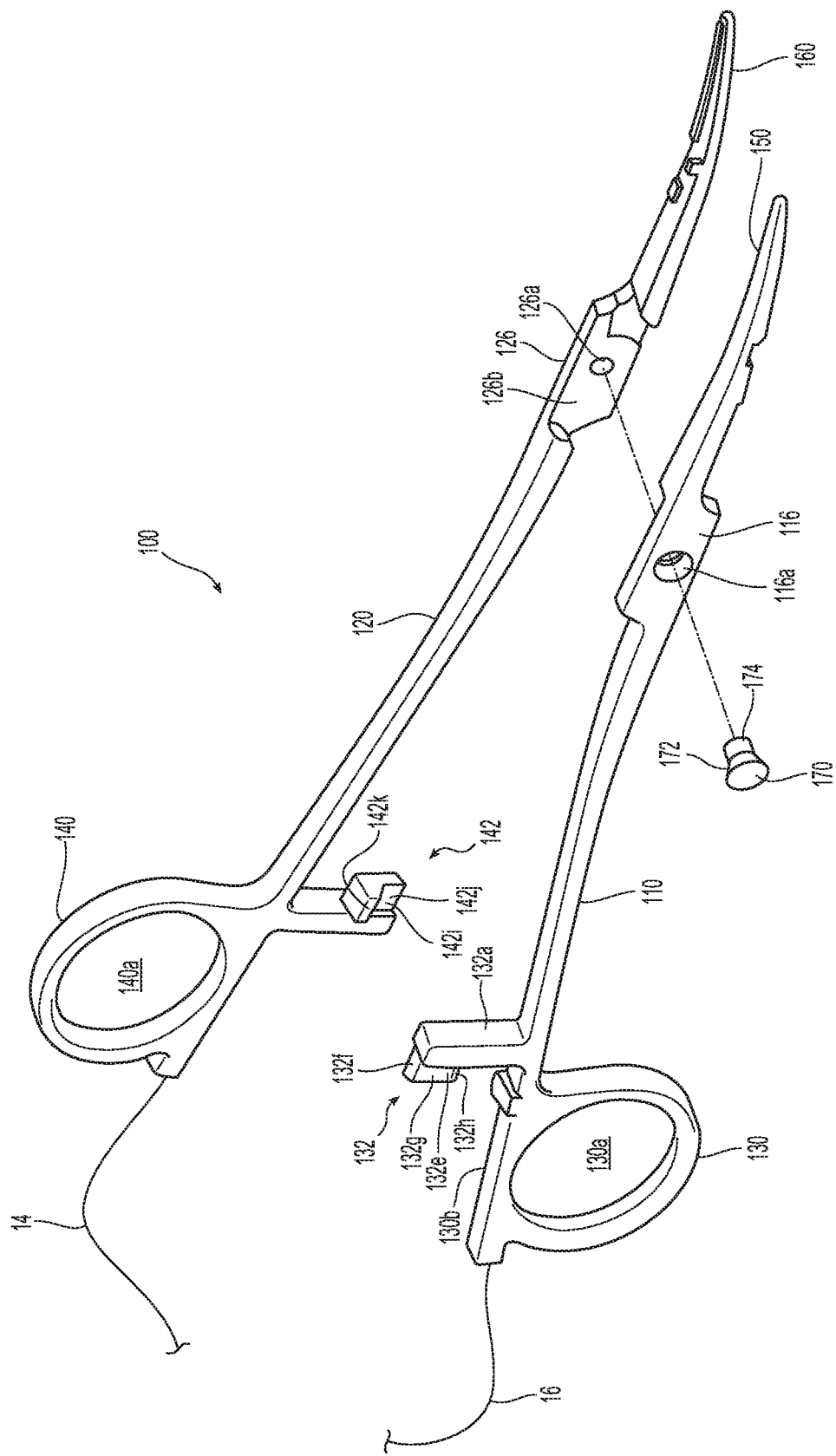
FIG. 2 is a perspective view of the forceps of FIG. 1 with parts separated.

A pivot pin 170 is positioned through the openings 116a and 126a defined in the intersection portions 116 and 126 of the first and second shaft members 110 and 120 such that movement of the first and second handle members 130 and 140 effect corresponding movement of the first and second jaw members 150 and 160 relative to each other. As best seen in FIG. 2, the pivot pin 170 includes a substantially semispherical head 172 disposed in the opening 116a of the first shaft member 110 and a cylindrical shaft 174 extending through the opening 126a defined in the second shaft member 120 such that the second shaft member 120 pivots about the cylindrical shaft 174 about an "x" axis (FIG. 1) and the first shaft member 110 is pivotable about the semispherical head 172.

The first and second jaw members 150 and 160 extend distally from the intersection portions 116 and 126 of the first and second shaft members 110 and 120. Proximal portions 150a and 160a of the first and second jaw members 150 and 160 extend longitudinally from the intersection portions 116 and 126, and distal portions 150b and 160b include curved first and second tissue contacting surfaces 154 and 164, respectively, that distally extend longitudinally and laterally away from the proximal portions 150a and 160a of the first and second jaw members 150 and 160.

Figure 4:
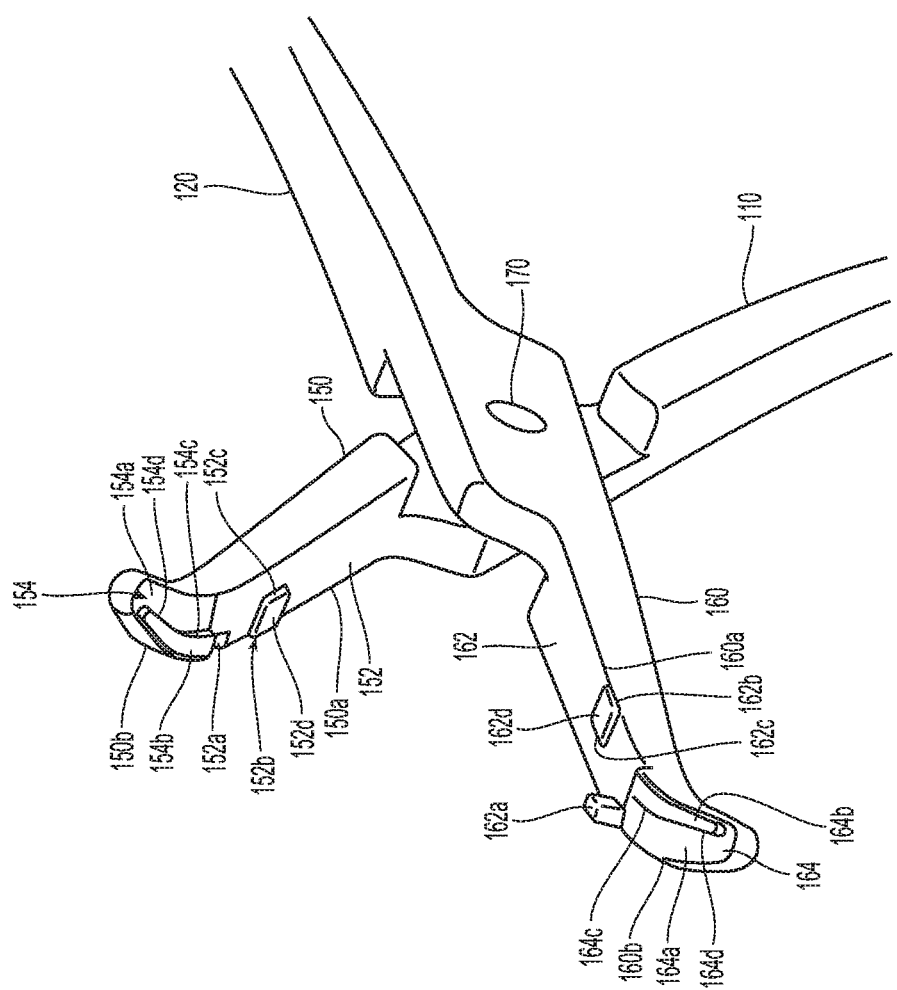
FIG. 4 an enlarged, perspective view of a distal end portion of the forceps of FIG. 1.

As best seen in FIG. 4, the proximal portion 150a of the first jaw member 150 includes a substantially flat inner surface 152, a slot 152a defined in an outer edge of the inner surface 152 and disposed adjacent to the distal portion 150b of the first jaw member 150, and a jaw guide 152b disposed on the inner surface 152 and having an oblique wall 152c extending from the inner surface 152 of the first jaw member 150 to a raised surface 152d of the jaw guide 152b. The proximal portion 160a of the second jaw member 160 includes a substantially flat inner surface 162 and a tab 162a extending from an outer edge of the inner surface 162 that is substantially aligned with the slot 152a of the first jaw member 150. Together, the slot 152a and the tab 162a act as a positioning mechanism to ensure that the first and second jaw members 150 and 160 are properly aligned when approximated. The proximal portion 160a also includes a jaw guide 162b disposed on the inner surface 162 and having an oblique walls 162c extending from the inner surface 162 of the second jaw member 160 to a raised surface 162d of the jaw guide 162b. The oblique walls 152c and 162c are complementary in shape and are aligned with each other. The oblique walls 152c and 162c and/or the raised surfaces 152d and 162d are configured to mate with each other upon movement of the first and second handle members 130 and 140 to control an open angle between the first and second jaw members 150 and 160, as described in further detail below.

The first and second tissue contacting surfaces 154 and 164 of the first and second jaw members 150 and 160 define complementary stepped surfaces which together grasp, seal, and/or cut tissue disposed therebetween. The first tissue contacting surface 154 includes a lower, base surface 154a and an upper, raised surface 154b that are laterally disposed relative to each other. An intermediate wall 154c extends perpendicular to, and connects, the base and raised surfaces 154a and 154b. A shear edge 154d is formed at the intersection of the raised surface 154b and the intermediate wall 154c.

Similarly, as described above with respect to the first tissue contacting surface 154, the second tissue contacting surface 164 includes a lower base surface 164a laterally disposed relative to an upper, raised surface 164b, and an intermediate wall 164c extending between and connecting the base and raised surfaces 164a and 164b. A shear edge 164d is disposed at the intersection of the raised surface 164b and the intermediate wall 164c.

The forceps 100 are formed from an electrically conductive material, e.g., a metal such as stainless steel, and is configured to conduct electrosurgical energy therethrough. The forceps 100 are covered in an insulative coating, such as a heat insulating paint, except on the tissue contacting surfaces 154 and 164 of the first and second jaw members 150 and 160. Accordingly, the forceps 110 are insulated at all surfaces that contact each other except at the tissue contacting surfaces 154 and 164 of the first and second jaw members 150 and 160 which together constitute a pair of electrodes for sealing tissue. In embodiments, the portions of the forceps 100 that contact other portions of the forceps 100, such as the intersection portions 116 and 126 and the first and second guide members 130 and 140 may be covered in a wear-resistant insulation material, such as an insert, sheet, or other suitable layer of material.

In one method of using the energy based surgical system 10 of the present disclosure, the forceps 100 is placed at a desired surgical site and the first and second jaw members 150 and 160 are positioned in an open position around desired tissue and/or vessel(s). As shown in FIG. 1, in the open position, the first and second handle members 130 and 140 and the first and second jaw members 150 and 160 are spaced apart from each other. As discussed above, the first and second jaw members 150 and 160 are movable relative to each other in response to movement of the first and second handle members 130 and 140.

The forceps 100 is moved into a first, approximated position by pivoting at least one of the first and second handle members 130 and 140 towards the other about the "x" axis to grasp and/or seal tissue disposed between the first and second jaw members 150 and 160. As shown in FIGS. 5A and 5B, as the first and second handle members 130 and 140 are moved vertically towards one another in the direction of arrows A and B, respectively, the convex plate 116f of the first elongated shaft member 110 abuts the inner surface 126b of the second elongated shaft member 120 so that the first and second elongated shaft members 110 and 120 are only rotatable about the "x" axis. Upon further closing, as shown in FIGS. 6A-6E, the convex plate 116f of the first elongated shaft member 110 contacts the concave plate 126c of the second elongated shaft member 120 (FIG. 6B) at about the same time that the inner surfaces 132e and 142e of the first and second guide members 130 and 140 (FIG. 6C) contact each other so that the first and second elongated shaft members 110 and 120 continue to rotate only about the "x" axis. As shown in FIG. 6D, the first and second guide members 130 and 140 may be latched together by locking the recessed upper surfaces 132h and 142h of the first and second guide members 130 and 140 relative to each other. In this first approximated position, as shown in FIGS. 6E and 6F, the first and second jaw members 150 and 160 are approximated such that the slot 152a of the first jaw member 150 receives the tab 162a of the second jaw member 160, and the tissue contacting surfaces 154 and 164 are diametrically opposed to one another such that the base surface 154a of the first jaw member 150 is aligned with the raised surface 164b of the second jaw member 160 and the raised surface 154b of the first jaw member 150 is aligned with the base surface 164a of the second jaw member 160.

In the first approximated position, the electrosurgical energy source 12 (FIG. 1) may be activated to apply electrosurgical energy to tissue grasped between the first and second tissue contacting surfaces 154 and 164 of the first and second jaw members 150 and 160. The electrosurgical energy source 12 may be manually activated/deactivated by actuating a trigger, button, foot pedal, among other switches within the purview of those skilled in the art.

When sealing is complete and the electrosurgical energy source 12 is shut off, the first and second handle members 130 and 140 may be returned to the open position (FIG. 1) to release tissue held between the first and second tissue contacting surfaces 154 and 164 of the first and second jaw members 150 and 160, or the first and second jaw members 150 and 160 may be moved to a second approximated position to cut the tissue disposed therebetween.

Figure 7A:
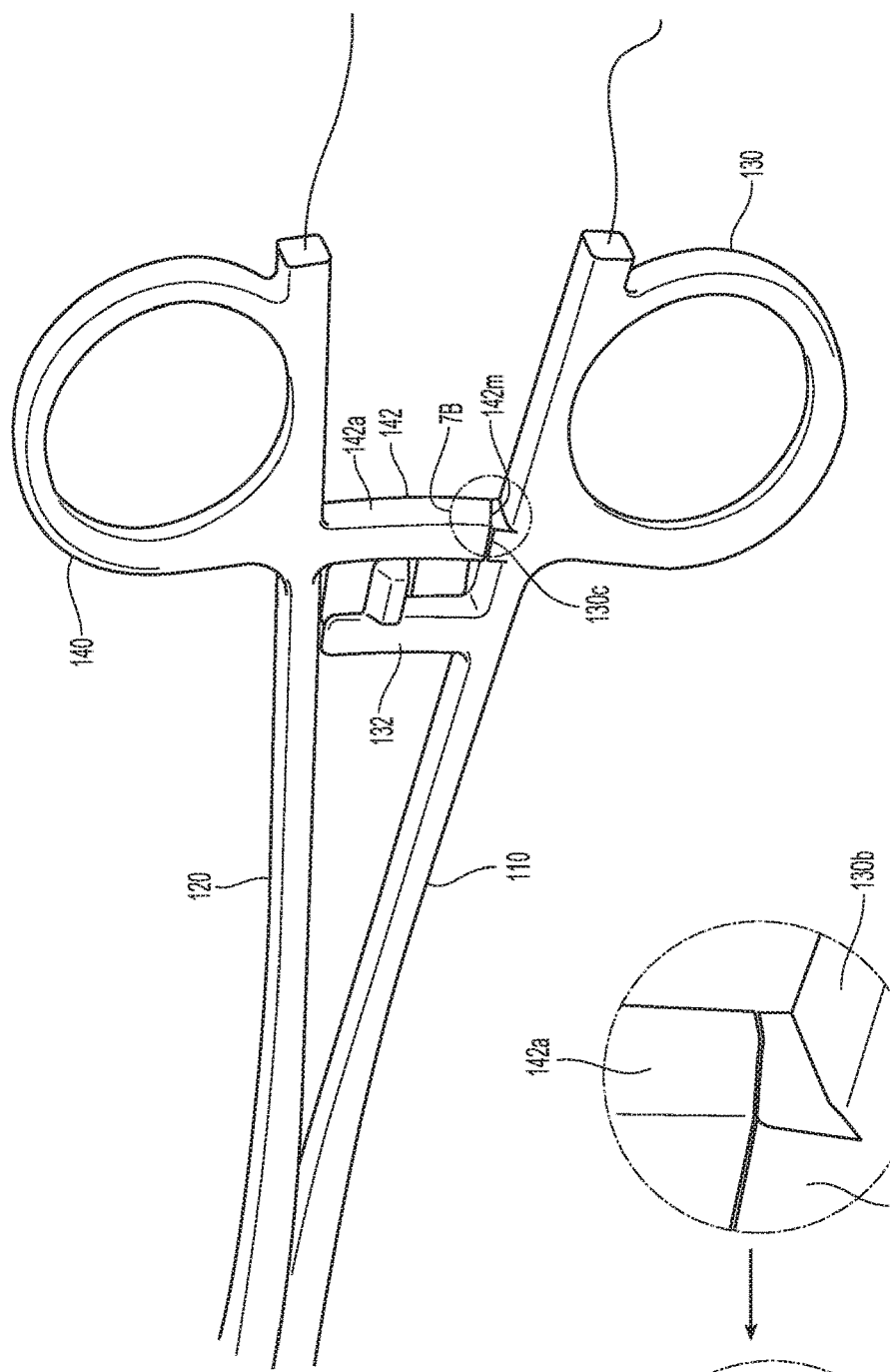
FIG. 7A is a side, perspective view of a proximal end portion of a forceps in accordance with another embodiment of the present disclosure.
Figure 7B:
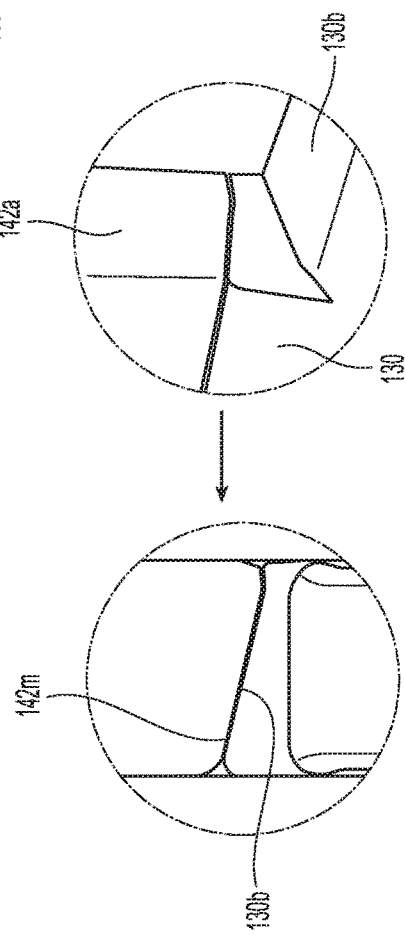
FIG. 7B is an enlarged view of a portion of the forceps of FIG. 7A shown along the area of detail 7B identified in FIG. 7A.
Figure 7C:
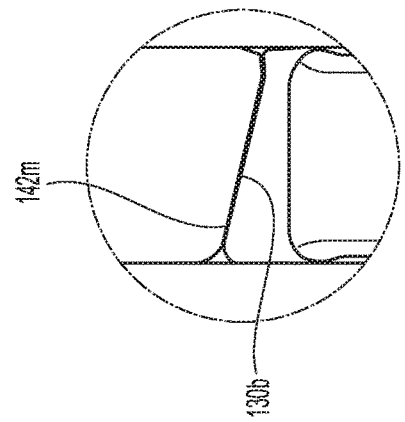
FIG. 7C is an enlarged front view of the portion of the forceps of FIG. 7B.

Alternatively, as shown in FIGS. 7A-7C, the electrosurgical energy source 12 (FIG. 1) may be automatically activated/deactivated upon movement of the first and second handle members 130 and 140 relative to each other. The electrosurgical energy source 12 is activated by pressing a bottom surface 142m of the body portion 142a of the second guide member 142 into contact with an inner surface 130c of the first handle member 130 to close the electrical circuit and energize the tissue contacting surfaces of the first and second jaw members 150 and 160 (FIG. 6A) to seal tissue disposed therebetween. In such embodiments, the bottom surface 142m of the body portion 142a of the second guide member 142 and the corresponding portion of the inner surface 130c of the first handle member 130 is free of insulative material. The electrosurgical energy source 12 is deactivated when the first and second handle members 130 and 140 are opened or moved to the second approximated position.

Figure 8A:
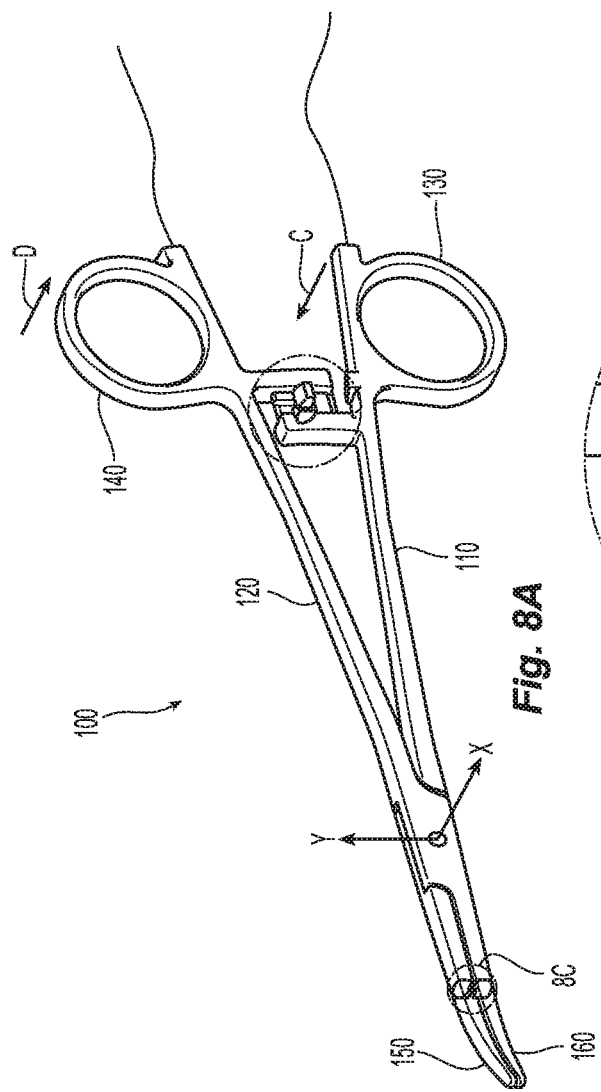
FIG. 8A is a side, perspective view of the forceps of FIG. 1 during movement from the first approximated position to a second approximated position.
Figure 8B:
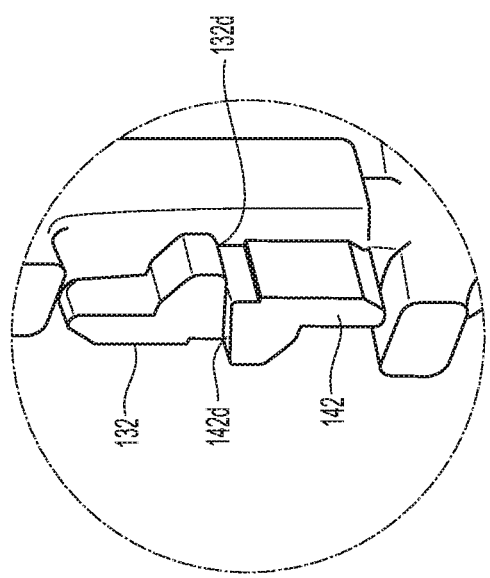
FIG. 8B is an enlarged view of a portion of the forceps of FIG. 8A shown along the area of detail 8B identified in FIG. 8A.
Figure 8C:
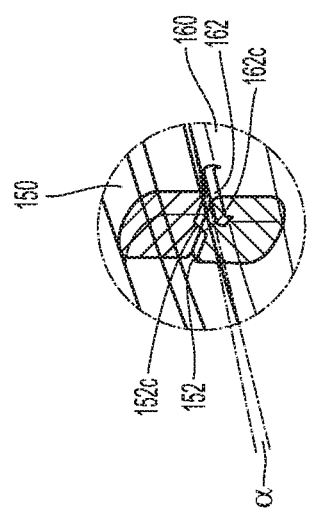
FIG. 8C is an enlarged view of a portion of the forceps of FIG. 8A shown along the area of detail 8C identified in FIG. 8A.
Figure 9:
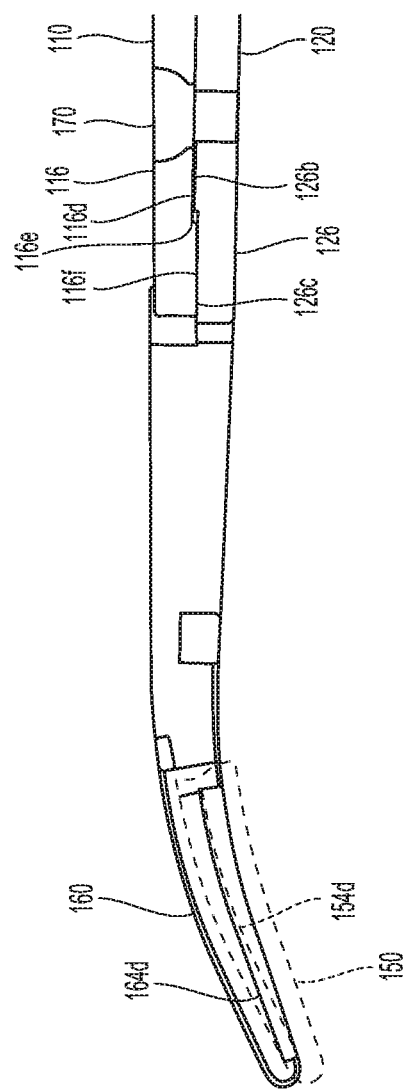
FIG. 9 is a top view, in partial cross-section, of the forceps of FIG. 8A in the second approximated position.

As shown in FIGS. 8A-8C, to move the forceps 100 to the second approximated position, the first and second handle members 130 and 140 are pressed in the directions of arrows C and D, respectively, and pivot around a "y" axis which is substantially perpendicular to the "x" axis such that the upper surfaces 132d and 142d of the first and second guide members 132 and 142 abut and substantially align (FIG. 8B). The inner surface 126b of the second elongate shaft 120 presses against the cam face 116e of the first elongated shaft 110 during movement of the first and second handle members 130 and 140 to prevent the first and second elongated shaft members 110 and 120 from moving in other directions (see e.g., FIG. 9). This lateral movement of the first and second handle member 130 and 140 causes corresponding movement of the first and second jaw members 150 and 160 such that the oblique walls 152c and 162c of the jaw guides 152b and 162b slide relative to each other (FIG. 8C) to open the first and second jaw members 150 and 160 at an angle "α" with respect to each other. At the same time, the shear edges 154d and 164d of the tissue contacting surfaces 154 and 164 start to cut tissue (not shown) from a leading end portion of the first and second jaw members 150 and 160. As shown in FIG. 9, in the second, approximated position, the oblique distal portion 116d of the intersection portion 116 of the first elongated shaft member 110 abuts the inner surface 126b of the intersection portion 126 of the second elongated shaft member 120 and the tissue contacting surfaces 154 and 164 are laterally offset with respect to each another such that the shear edges 154d and 164d cross each other to cut tissue. When cutting is complete, the first and second handle members 130 and 140 are moved back to the open position (FIG. 1).

As shown in FIGS. 10A-13C, the relationship between the flat and raised surfaces of the first and second tissue contacting surfaces 152 and 162 may be arranged in a variety of configurations to change the force and/or distance required to move the first and second handle members 130 and 140 from the first approximated position to the second approximated position. For example, as shown in FIGS. 10A-10C, leading end portions 151' and 161' of first and second tissue contacting surfaces 152' and 162' of first and second jaw members 150' and 160' are configured to be at an angle with respect to each other when in the first approximated position, and to start cutting tissue at the leading end portions 151' and 161' of the first and second tissue contacting surfaces 152' and 162'. As shown in FIGS. 11A-11C, first and second tissue contacting surfaces 152" and 162" are configured to be substantially parallel in the first approximated position and to start cutting tissue at leading end portions 151" and 161" of the first and second tissue contacting surfaces 152" and 162" of the first and second jaw members 150" and 160". The first and second jaw members 150' and 160' of FIGS. 10-10C require minimal force to cut tissue, but require movement over a greater distance than the first and second jaw members 150" and 160" of FIGS. 11A-11C, which require more force to cut but less lateral movement. The first and second tissue contacting surfaces 152''' and 162''' of the first and second jaw members 150''' and 160''' of FIGS. 12A-12C cut tissue along the entire length of the shear edges of the first and second tissue contacting surfaces 152''' and 162''' at the same time and require more force and less lateral movement. The first and second jaw members 150'''' and 160'''' of FIGS. 13A-13C are configured to start cutting tissue from the trailing end portions 153'''' and 163'''' of the first and second tissue contacting surfaces 152'''' and 162'''', the angle that the jaw members 150'''' and 160'''' open being inverse to that of FIGS. 10A-10C.

Figures 14A, 14B:
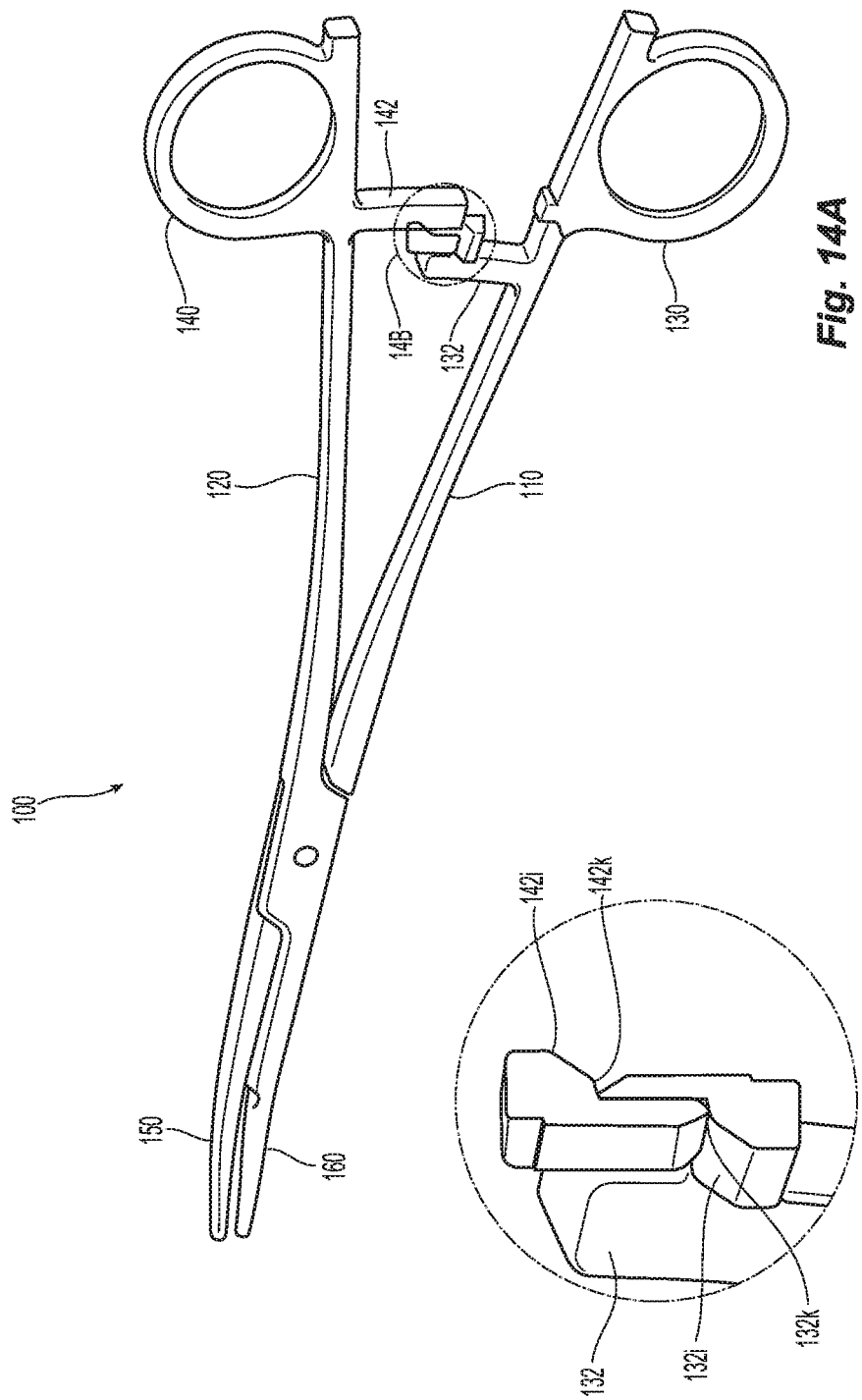
FIG. 14A is a side perspective view the forceps of FIG. 1 with misaligned handle members.
FIG. 14B is an enlarged view of a portion of the forceps of FIG. 14A shown along the area of detail 14B identified in FIG. 14A.

As shown in FIGS. 14A-14B, the first and second guide members 132 and 142 of the first and second handle members 130 and 140 prevent misalignment of the first and second jaw members 150 and 160 during closure of the forceps 100. If the first and second handle members 130 and 140 are misaligned, the protrusive upper surfaces 132k and 142k on the outer surfaces 132i and 142i of the first and second guide members 132 and 142 prevent movement of the first and second handle members 130 and 140 toward the first approximated position.

Figure 16:
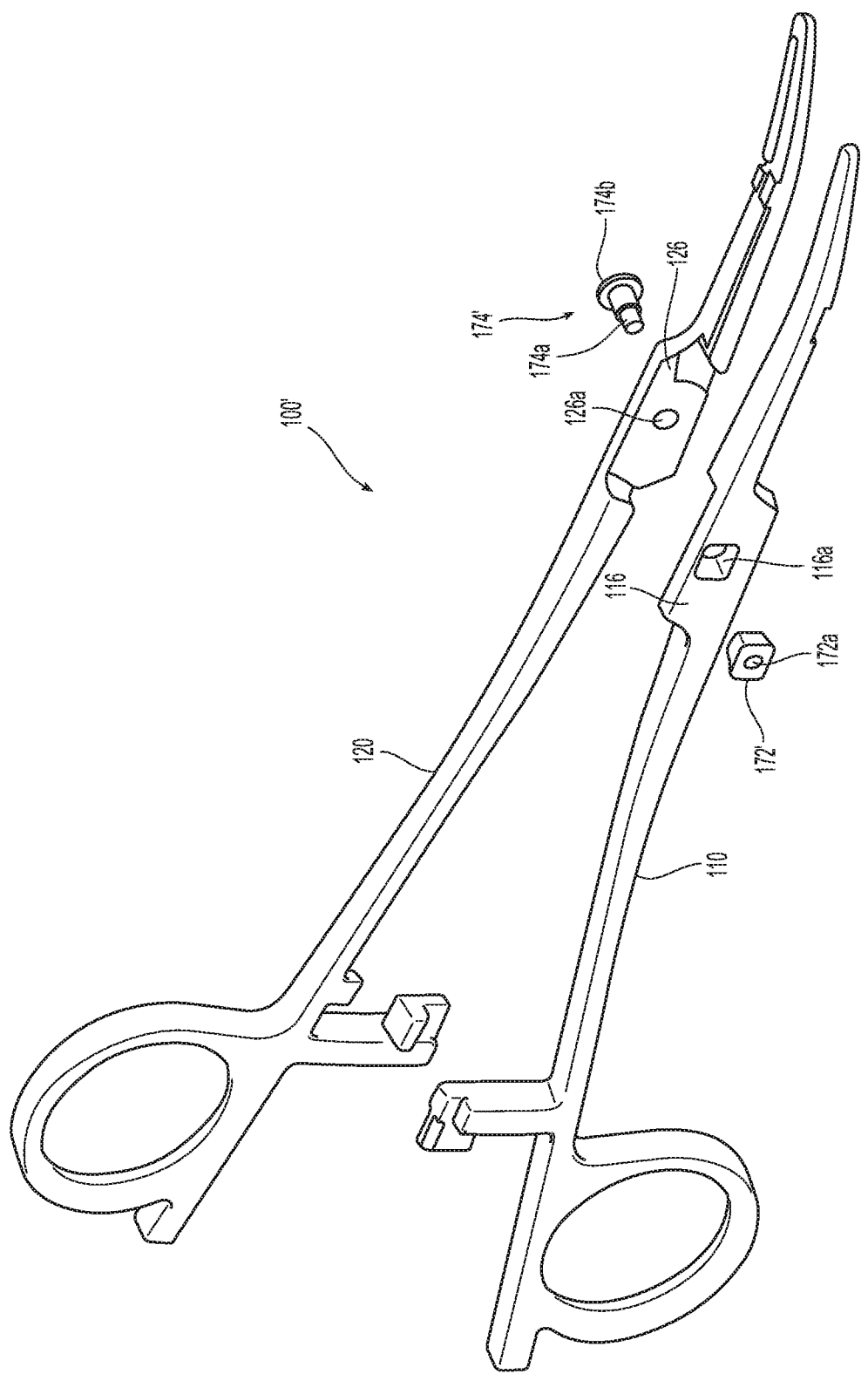
FIG. 16 is a side perspective view of the forceps of FIG. 15A with parts separated.

Turning now to FIGS. 15A-16, a forceps 100' in accordance with another embodiment of the present disclosure includes a first elongated shaft member 110 pivotably connected to a second elongated shaft member 120 via a pivot pin 170'. The pivot pin 170' includes a hemi-cylindrical head 172' defining an opening 172a therethrough and a cylindrical shaft 174' including a first end 174a configured to be secured within the opening 172a of the head 172' and a flanged second end 174b. The hemi-cylindrical head 172' is positioned in the opening 116a defined in the first intersection portion 116 of the first elongated shaft member 110 and the shaft 174' is positioned through the opening 126a defined in the intersection portion 126 of the second elongated shaft member 120 such that the flanged second end 174b secures the shaft 174' to the second elongated shaft member 120. The hemi-cylindrical head 172' ensures that the first elongated shaft member 110 can only rotate around an axis that is substantially perpendicular to the "x" axis during cutting and cannot sway in other directions, and the shaft 174' ensures that the second elongated shaft member 120 is rotatable only about the "x" axis. In some embodiments, as shown in FIG. 15B, an insulation insert or sheet 176 may be positioned between the intersection portions 116 and 126 of the first and second elongated shaft members 110 and 120 to electrically isolate the first and second elongated shaft members 110 and 120 from each other.

The embodiments disclosed herein may also be configured to work with robotic surgical systems and what is commonly referred to as "Telesurgery." Such systems employ various robotic elements to assist the operator and allow remote operation (or partial remote operation) of surgical instrumentation. Various robotic arms, gears, cams, pulleys, electric and mechanical motors, etc. may be employed for this purpose and may be designed with a robotic surgical system to assist the operator during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep a subject (e.g., a patient) for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 17:
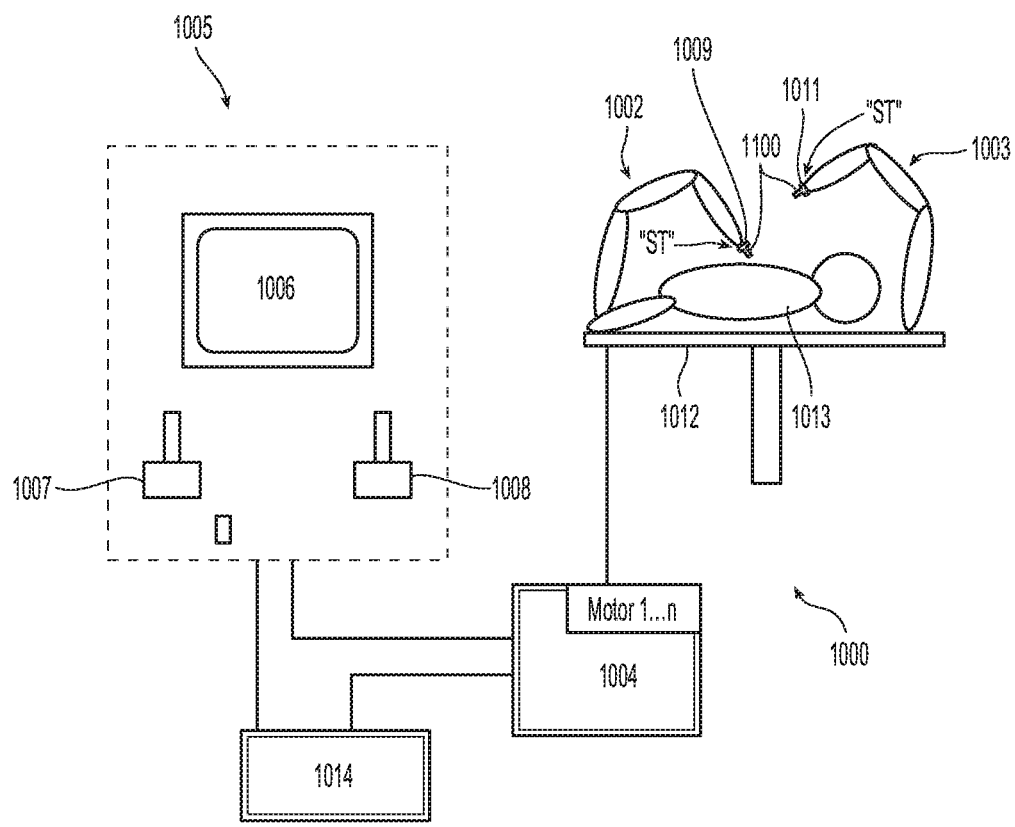
FIG. 17 is a schematic illustration of a work station configured for use with a forceps of the present disclosure.

As shown in FIG. 17, a medical work station is shown generally as work station 1000 and generally may include a plurality of robot arms 1002 and 1003; a control device 1004; and an operating console 1005 coupled with control device 1004. Operating console 1005 may include a display device 1006, which may be set up in particular to display three-dimensional images; and manual input devices 1007 and 1008, by means of which an operator (not shown), for example a surgeon, may be able to telemanipulate robot arms 1002 and 1003 in a first operating mode.

Each of the robot arms 1002 and 1003 may include a plurality of members, which are connected through joints, and an attaching device 1009 and 1011, to which may be attached, for example, a surgical tool "ST" supporting an end effector 1100, in accordance with any one of several embodiments disclosed herein, as will be described in greater detail below.

Robot arms 1002 and 1003 may be driven by electric drives (not shown) that are connected to control device 1004. Control device 1004 (e.g., a computer) may be set up to activate the drives, in particular by means of a computer program, in such a way that robot arms 1002 and 1003, their attaching devices 1009 and 1011 and thus the surgical tool (including end effector 1100) execute a desired movement according to a movement defined by means of manual input devices 1007 and 1008. Control device 1004 may also be set up in such a way that it regulates the movement of robot arms 1002 and 1003, and/or of the drives.

Medical work station 1000 may be configured for use on a patient 1013 lying on a patient table 1012 to be treated in a minimally invasive manner by means of end effector 1100. Medical work station 1000 may also include more than two robot arms 1002 and 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to control device 1004, in which are stored, for example, pre-operative data from patient/living being 1013 and/or anatomical atlases.

While several embodiments of the disclosure have been shown in the drawings and described herein, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

What is claimed is:

1. An electrosurgical forceps, comprising:
an end effector including first and second jaw members, the first jaw member having a proximal portion including an inner surface having a first jaw guide member disposed thereon and a distal portion including a first tissue contacting surface having stepped surfaces, the second jaw member having a proximal portion including an inner surface having a second jaw guide member disposed thereon and a distal portion including a second tissue contacting surface having stepped surfaces, the inner surfaces of the proximal portions of the first and second jaw members facing each other, each of the first and second tissue contacting surfaces having a shear edge disposed between the stepped surfaces,
the first and second jaw members vertically movable between an open position and a first approximated position in which the first and second tissue contacting surfaces vertically oppose and laterally align with each other, and laterally movable between the first approximated position and a second approximated position to laterally displace the first and second tissue contacting surfaces with respect to each other, the first and second jaw guide members controlling an open angle between the first and second jaw members during movement between the first approximated position and the second approximated position; and
first and second elongated shaft members that cooperate to define the end effector, the first jaw member disposed on a distal end portion of the first elongated shaft member and the second jaw member disposed on a distal end portion of the second elongated shaft member, the first and second elongated shaft members coupled together by a pivot pin extending through openings defined in respective first and second intersection portions of the first and second elongated shaft members, at least one of the first and second elongated shaft members pivotable with respect to the other of the first and second shaft members about at least two axes.

2. The electrosurgical forceps according to claim 1, wherein each of the first and second tissue contacting surfaces includes a leading end portion and a trailing end portion, the stepped surface of each of the first and second tissue contacting surfaces includes a base surface laterally disposed relative to a raised surface, the base and raised surfaces connected by an intermediate wall that forms the shear edge at an intersection with the raised surface, the shear edge extending from the leading end portion to the trailing end portion.

3. The electrosurgical forceps according to claim 1, wherein the distal portions of the first and second jaw members curve longitudinally and laterally away from the proximal portions of the first and second jaw members.

4. The electrosurgical forceps according to claim 1, wherein the first and second guide members include opposed oblique walls that contact and slide laterally relative to each other during movement from the first approximated position to the second approximated position.

5. The electrosurgical forceps according to claim 1, wherein the inner surface of the proximal portion of the first jaw member includes a slot defined in an outer edge thereof and the inner surface of the proximal portion of the second jaw member includes a complementary tab extending from an outer edge thereof for reception within the slot.

6. The electrosurgical forceps according to claim 1, wherein the pivot pin includes a semispherical head disposed within the opening defined in the first intersection portion and a cylindrical shaft extending through the opening defined in the second intersection portion.

7. The electrosurgical forceps according to claim 1, wherein the first intersection portion includes an inner surface having a substantially flat proximal portion, an oblique distal portion, and a convex portion disposed at a distal end of the oblique distal portion, and the second intersection portion includes a substantially flat inner surface and a concave surface disposed at a distal end of the substantially flat inner surface.

8. The electrosurgical forceps according to claim 7, wherein the first intersection portion includes a cam face disposed between the substantially flat proximal portion and the oblique distal portion.

9. The electrosurgical forceps according to claim 1, wherein proximal end portions of the first and second elongated shaft members of the forceps include first and second handle members, respectively, the first handle member including a first guide member and the second handle member including a second guide member, each of the first and second guide members including a body portion extending generally vertically from an inner surface of the respective first and second handle member, a leg portion extending substantially perpendicularly from the body portion, and a gap defined between an upper surface of the leg portion and the inner surface of the respective first and second handle member, the leg portions of the first and second guide members longitudinally aligned and laterally offset with respect to each another.

10. The electrosurgical forceps according to claim 9, wherein when the first and second jaw members are in the open position, the first and second guide members are spaced apart, and when the first and second jaw members are in the first approximated position, the inner surfaces of the leg portions of the first and second guide members contact each other.

11. The electrosurgical forceps according to claim 10, wherein when the first and second jaw members are in the first approximated position, the inner surfaces of the legs portions of the first and second guide members are locked relative to each other.

12. The electrosurgical forceps according to claim 9, wherein when the first and second jaw members are in the first approximated position, a bottom surface of the body portion of the first guide member contacts an inner surface of the second elongated shaft member.

13. The electrosurgical forceps according to claim 9, wherein when the first and second jaw members are in the second approximated position, the upper surfaces of the leg portions of the first and second guide members contact each other.

14. The electrosurgical forceps according to claim 9, wherein outer surfaces of the leg portions of the first and second guide members each include a protrusive surface to prevent movement of the first and second handle members relative to each other when the first and second jaw members are moved from the open position to the first approximated position and the outer surfaces are aligned with each other.

15. A method of treating tissue comprising the steps of:
vertically moving at least one of first and second handle members of an electrosurgical forceps towards the other of the first and second handle members to move first and second jaw members of the electrosurgical forceps from an open position to a first approximated position in which first and second tissue contacting surfaces are vertically opposed and substantially aligned with each other to grasp tissue therebetween; and
laterally moving at least one of the first and second handle members towards the other of the first and second handle members from the first approximated position to a second approximated position such that oblique walls of first and second jaw guide members disposed on inner surfaces of the first and second jaw members contact and slide relative to each other to open the first and second jaw members at an angle with respect to each other and to cut tissue disposed between the first and second jaw members by crossing shear edges defined on the first and second tissue contacting surfaces.

16. An electrosurgical forceps, comprising:
an end effector including first and second jaw members, the first jaw member having a proximal portion including an inner surface having a first jaw guide member disposed thereon and a distal portion including a first tissue contacting surface having stepped surfaces, the second jaw member having a proximal portion including an inner surface having a second jaw guide member disposed thereon and a distal portion including a second tissue contacting surface having stepped surfaces, the inner surfaces of the proximal portions of the first and second jaw members facing each other, each of the first and second tissue contacting surfaces having a shear edge disposed between the stepped surfaces,
the first and second jaw members vertically movable between an open position and a first approximated position in which the first and second tissue contacting surfaces vertically oppose and laterally align with each other, and laterally movable between the first approximated position and a second approximated position to laterally displace the first and second tissue contacting surfaces with respect to each other, the first and second jaw guide members controlling an open angle between the first and second jaw members during movement between the first approximated position and the second approximated position, the first and second guide members including opposed oblique walls that contact and slide laterally relative to each other during movement from the first approximated position to the second approximated position.

\* \* \* \* \*